(12) United States Patent
Lösel et al.

(10) Patent No.: US 6,395,776 B1
(45) Date of Patent: May 28, 2002

(54) PESTICIDES

(75) Inventors: Peter Lösel, Monheim; Gunther Penners, Leverkusen; Maria-Giuliana Cianciulli-Teller, Wuppertal, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/000,356

(22) PCT Filed: Jul. 22, 1996

(86) PCT No.: PCT/EP96/03220

§ 371 (c)(1),
(2), (4) Date: Jan. 28, 1998

(87) PCT Pub. No.: WO97/05778

PCT Pub. Date: Feb. 20, 1997

(30) Foreign Application Priority Data

Aug. 3, 1995 (DE) .......................................... 195 28 529

(51) Int. Cl.[7] .............................................. A01N 53/00
(52) U.S. Cl. .................. 514/531; 424/84; 424/405; 424/406; 424/407; 424/409; 424/410; 424/411; 424/DIG. 10; 514/359; 514/520; 514/521; 514/558; 514/560; 514/679; 514/739; 514/918; 514/919
(58) Field of Search ............................ 424/84, 405–407, 424/409–411, 417, 419, 420, DIG. 10; 514/359, 520, 521, 531, 558, 560, 679, 739, 918–919, 920

(56) References Cited

U.S. PATENT DOCUMENTS

| | | | | |
|---|---|---|---|---|
| 4,456,587 A | | 6/1984 | Keith | .......................... 424/78 |
| 4,837,216 A | * | 6/1989 | Mehlhorn et al. | .......... 514/241 |
| 5,364,969 A | | 11/1994 | Sakurada et al. | |
| 5,759,561 A | | 6/1998 | Angst et al. | |
| 5,925,368 A | * | 7/1999 | Voris et al. | .................. 424/405 |

FOREIGN PATENT DOCUMENTS

| | | |
|---|---|---|
| DE | 3107129 | 12/1981 |
| DE | 4136832 | 5/1992 |
| DE | 4330591 | 4/1994 |
| EP | 376888 | 7/1990 |
| EP | 0376888 | 7/1990 |
| GB | 2058569 | 4/1981 |
| GB | 2072013 | * 9/1981 |

* cited by examiner

Primary Examiner—Neil S. Levy
(74) Attorney, Agent, or Firm—Norris McLaughlin & Marcus

(57) ABSTRACT

New pesticidal compositions which comprise
- at least one signal substance,
- at least one UV absorber which is only sparingly miscible with water,
- at least one unsaturated oil which is only sparingly miscible with water and,
- if desired, pesticidally active compounds and/or additives, a process for the preparation of the new compositions, and their use for controlling insects and undesirable representatives of the order Acarina.

13 Claims, No Drawings

PESTICIDES

The present invention relates to novel compositions for controlling harmful insects and representatives of the order Acarina, a process for the preparation of these compositions, and their use in agriculture, forestry and horticulture.

When controlling phytophagous animal pests with the aid of pesticides, one attempts to minimize contamination of the plants to be protected and their environment, including the soil in which they grow. Moreover, beneficial animals and warm-blooded species are to be adversely affected by the pesticidally active compounds as little as possible. However, in contrast, the pests to be controlled are to be exposed to the pesticidally active compounds as much as possible so that the pests can take up sufficient amounts of the active compounds by contact action, as stomach poisons or via the gas phase.

When controlling insects, the abovementioned conditions can be met for example by combining signal substances such as pheromones, kairomones or attractants, which have an attractant action on insects, with insecticidally active compounds and applying the resulting mixtures to the stand to be protected not in such a way that the entire area is covered, but only locally to sharply defined individual sites. Since the signal substances are released at the treated sites, the pests migrate to these sites, become contaminated with the pesticidally active compounds and are destroyed. This type of insect control is termed the "attract-and-kill" method.

In contrast, it is also possible to control insects with the aid of the so-called "confusion" strategy. When using this method, the amount of pheromones introduced into the plant stand to be protected is so large that the male insects are no longer capable of locating the female insects. This prevents the pests from breeding.

For the compositions used in the two control strategies to develop a sufficiently long-term action, the formulations in question must comprise the attractants in such a form that, on the one hand, they can be released in a controlled manner but, on the other hand, are protected against environmental factors such as light, oxygen and the weather.

A large number of preparations based on the above-described principles of controlling animal pests have already been disclosed. One attempts to protect the sensitive active compounds against undesirable degradation by means of a variety of measures.

For example, EP-A 0 055 475 discloses that male insects of the species Cossus cossus can be controlled with the aid of (Z)-5-dodecen-1-yl acetate, if appropriate in the form of a mixture with (Z)-3-decen-1-yl acetate, (Z)-3-dodecen-1-yl acetate and/or (E)-5-dodecen-1-yl acetate. The attractant, or the mixtures of the active components, are applied in solvents which have a low vapour pressure, such as oils or fats, or else, if appropriate, as a mixture with antioxidants and UV stabilizers in the form of an adsorbate on inert solids.

Furthermore, GB-PA 2 064 323 describes insecticides based on pheromones in which the signal :substances and UV stabilizers and additional additives such as antioxidants are fixed onto a combination of absorbing and adsorbing solids. However, the disadvantage of these preparations is their relatively poor resistance to weathering despite the stabilizing additives which they comprise and the fact that the active compounds are therefore decomposed or leached out after a relatively short time.

Furthermore, it has already been disclosed to employ combinations of attractants and insecticides for pest control in microencapsulated form or bound in water-soluble polymers (cf. JP-A 59-7101 and "Advances in Pesticide Formulation Technology" 1984, Chapter 11, pages 151–162). In the preparation of these microcapsules, a procedure is followed in which the active compounds are dissolved in an oil phase, the resulting mixture is emulsified in water and the emulsion is subsequently encapsulated. Controlled release of the attractant and, in addition, its protection against environmental factors are thereby achieved. The disadvantage of this process is, however, the complicated microencapsulation process. Moreover, the attractants are not always sufficiently stabilized against environmental factors, despite the encapsulation, because the thin capsule wall does not provide sufficient protection against photochemical degradation.

According to GB-A 2 141 932, preparations which comprise pheromones, if appropriate as a mixture with UV absorbers and other additives, in liquid or semi-liquid, liquid, water-resistant polymers which protect against UV radiation, can be used as pesticides. While the active components remain stable over a sufficiently long period in these formulations, the amount of active compound which diffuses out does not always guarantee a sufficiently high degree of efficacy.

EP-A 0 376 888 discloses that formulations which are composed mostly of one or more permanently liquid UV absorbers, besides insecticides and attractants and customary additives, and which are present in viscous form which remains permanently uncured are also suitable for controlling pests. The very high content of UV-absorbing substances protects the attractants in these formulations against photodegradation over a prolonged period. However, the use under realistic conditions causes problems since the UV absorbers are, as a rule, highly stable and are not degraded, or are degraded only very slowly. If the formulation is applied regularly over several years, it is therefore accumulated in the area under cultivation which has been treated.

Furthermore, WO 87-04 591 discloses compositions for controlling spider mites. The formulations are composed of a substrate which comprises attractants such as Nerodiol and Farnesol, furthermore insecticidally active compounds and also oils which are added in the form of emulsions. The attractants are released from these substrates in a controlled manner. However, the disadvantage is that no long-term action is achieved when using these compositions. Rather, achieving satisfactory control requires regular subsequent treatments.

J. Entomol. Sci. Vol. 25, No. 4, 581–586, (1990) describes pheromone—and insecticide—comprising preparations for controlling the cotton boll weevil (Anthonomus grandis). As an essential component, the compositions comprise cotton seed oil, which promotes feeding of the pest and therefore has a beneficial effect on the uptake of active compound. However, the fact that this vegetable oil does not contribute to stabilizing the formulation against environmental effects is unfavourable.

Finally, it has been disclosed that oils in attractant-comprising preparations can act as solvents for active compounds (cf. WO 87-04 591, EP-A 0 055 475 and "Advances in Pesticide Formulation Technology 1984, Chapter 11, pages 151 to 162). The active compounds, however, are not stabilized against undesirable degradation.

There have now been found new pesticidal compositions which comprise
- at least one signal substance,
- at least one UV absorber which is only sparingly miscible with water,
- at least one unsaturated oil which is only sparingly miscible with water and
- if appropriate, pesticidally active compounds and/or additives.

Furthermore, it has been found that compositions according to the invention can be prepared by
a) dispersing at least one signal substance, at least one UV absorber which is only sparingly miscible with water and, if appropriate, pesticidally active compounds and/or additives in at least one unsaturated oil which is only sparingly miscible with water and b) if appropriate, emulsifying this premix in water while adding surface-active substances.

Finally, it has been found that the compositions according to the invention are highly suitable for controlling harmful insects and undesirable representatives from the order Acarina in agriculture, forestry and horticulture.

It must be considered as extremely surprising that the compositions according to the invention, which comprise a mixture of UV absorber and unsaturated oil, protect the signal substances which are present and the pesticidally active compounds which may also be present, better against environmental degradation than prior-art compositions which comprise either only the unsaturated vegetable oil or merely the UV absorber.

The compositions according to the invention are distinguished by a series of advantages. For example, they allow specific and environmentally friendly pest control over a prolonged period. Furthermore, the attractants in these preparations are extremely stable even under unfavourable weather conditions.

The signal substances which may be present in the compositions according to the invention are all customary substances which have an attractant action on the pests to be controlled and which alter the behaviour of the latter. Signal substances which are preferably suitable are pheromones, kairomones and attractants. Examples of such substances which may be mentioned are the following:

Z-5-Decenyl acetate, dodecanyl acetate, Z-7-dodecenyl acetate, E-7-dodecenyl acetate, Z-8-dodecenyl acetate, E-8-dodecenyl acetate, Z-9-dodecenyl acetate, E-9-dodecenyl acetate, E-10-dodecenyl acetate, 11-dodecenyl acetate, Z-9,11-dodecadienyl acetate, E-9,11-dodecadienyl acetate, Z-11-tridecenyl acetate, E-11-tridecenyl acetate, tetradecenyl acetate, E-7-tetradecenyl acetate, Z-8-tetradecenyl acetate, E-8-tetradacenyl acetate, Z-9-tetradecenyl acetate, E-9-tetradecenyl acetate, Z-10-tetradecenyl acetate, E-10-tetradecenyl acetate, Z-11-tetradecenyl acetate, E-11-tetradecenyl acetate, Z-12-pentadecenyl acetate, E-12-pentadecenyl acetate, hexadecanyl acetate, Z-7-hexadecenyl acetate, Z-11-hexadecenyl acetate, E-11-hexadecenyl acetate, octadecanyl acetate, E,Z-7,9-dodecadienyl acetate, Z,E-7,9-dodecadienyl acetate, E,E-7,9-dodecadienyl acetate, Z,Z-7,9-dodecadienyl acetate, E,E-8,10-dodecadienyl acetate, E,Z-9,12-dodecadienyl acetate, E,Z-4,7-tri-decadienyl acetate, 4-methoxy-cinnamaldehyde, β-ionone, estragol, eugenol, indole, 8-methyl-2-decyl propanoate, E,E-9,11-tetradecadienyl acetate, Z,Z-9,12-tetradecadienyl acetate, Z,Z-7,11-hexadecadienyl acetate, E,Z-7,11-hexadecadienyl acetate, Z,E-7,11-hexadecadienyl acetate, E,E-7,11-hexadecadienyl acetate, Z,E-3,13-octadecadienyl acetate, E,Z-3,13-octadecadienyl acetate, E,E-3,13-octadecadienyl acetate, ethanol, hexanol, heptanol, octanol, decanol, Z-6-nonenol, E-6-nonenol, dodecanol, 11-dodecenol, Z-7-dodecenol, E-7-dodecenol, Z-8-dodecenol, E-8-dodecenol, E-9-dodecenol, Z-9-dodecenol, E-9,11-dodecadienol, Z-9,11-dodecadienol, Z,E-5,7-dodecadienol, E,E-5,7-dodecadienol, E,E-8,10-dodecadienol, E,Z-8,10-dodecadienol, Z,Z-8,10-dodecadienol, Z,E-8,10-dodecadienol, E,Z-7,9-dodecadienol, Z,Z-7,9-dodecadienol, E-5-tetradecenol, Z-8-tetradecenol, Z-9-tetradecenol, E-9-tetradecenol, Z-10-tetradecenol, Z-11-tetradecenol, E-11-tetradecenol, Z-11-hexadecenol, Z,E-9,11-tetradecadienol, Z,E-9,12-tetradecadienol, Z,Z-9,12-tetradecadienol, Z,Z-10,12-tetradecadienol, Z,Z-7,11-hexadecadienol, Z,E-7,11-hexadecadienol, (E)-14-methyl-8-hexadecen-1-ol, (Z)-14-methyl-8-hexadecen-1-ol, E,E-10,12-hexadecadienol, E,Z-10,12-hexadecadienol, dodecanal, Z-9-dodecenal, tetradecanal, Z-7-tetradecenal, Z-9-tetradecenal, Z-11-tetradecenal, E-11-tetradecenal, E-11,13-tetradecadienal, E,E-8,10-tetradecadienal, Z,E-9,11-tetradecadienal, Z,E-9,12-tetradecadienal, hexadecanal, Z-8-hexadecenal, Z-9-hexadecenal, Z-10-hexadecenal, E-10-hexadecenal, Z-11-hexadecenal, E-11-hexadecenal, Z-12-hexadecenal, Z-13-hexadecenal, (Z)-14-methyl-8-hexadecenal, (E)-14-methyl-8-hexadecenal, Z,Z-7,11-hexadecadienal, Z,E-7,11-hexadecadienal, Z,E-9,11-hexadecadienal, E,E-10,12-hexadecadienal, E,Z-10,12-hexadecadienal, Z,E-10,12-hexadecadienal, Z,Z-10,12-hexadecadienal, Z,Z-11,13-hexadecadienal, octadecanal, Z-11-octadecenal, E-13-octadecenal, Z-13-octadecenal, Z-5-decenyl-3-methyl butanoate disparlure: (+) cis-7,8-epoxy-2-methyloctadecane, seudenol: 3-methyl-2-cyclohexen-1-ol, sulcatol: 6-methyl-5-hepten-2-ol, ipsenol: 2-methyl-6-methylene-7-octen-4-ol, ipsdienol: 2-methyl-6-methylene-2,7-octadien-4-ol, grandlure I: cis-2-isopropenyl-1-methylcyclobutane-ethanol, grandlure II: Z-3,3-dimethyl-1-cyclohexane-ethanol, grandlure III: Z-3,3-dimethyl-1-cyclohexane-acetalde-hyde, grandlure IV: E-3,3-dimethyl-1-cyclohexane-acetaldehyde, cis-2-ver-benol: cis-4,6,6-trimethylbicyclo[3,1,1]hept-3-en-2-ol cucurbitacin, 2-methyl-3-buten-2-ol, 4-methyl-3-heptanol, cucurbitacin, 2-methyl-3-buten-2-ol, 4-methyl-3-heptanol, α-pinene: 2,6,6-trimethylbicyclo[3,1,1]hepten-2-ene, α-caryophyllene: 4,11,11-trimethyl-8-methylene-bicyclo[7,2,0]undecane, Z-9-tricosene, (α-multistriatin, 2-(2-endo,4-endo)-5-ethyl-2,4-dimethyl-6,8-dioxabicyclo[3,2,1]octane, methyleugenol: 1,2-dimethoxy-4-(2-propenyl)phenol, lineatin: 3,3,7-trimethyl-2,9-dioxatricyclo[3,3,1,0]nonane, chalcogran: 2-ethyl-1,6-dioxaspiro[4,4]nonane, frontalin: 1,5-dimethyl-6,8-dioxabicyclo[3,2,1]octane, endo-brevicomin: endo-7-ethyl-5-methyl-6,8-dioxabicyclo [3,2,1]octane, exo-brevicomin: exo-7-ethyl-5-methyl-6,8-dioxabicyclo[3,2,1]octane, (Z)-5-(1-decenyl) dihydro-2-(3H)-furanone, farnesol: 3,7,11-trimethyl-2,6,10-dodecatrien-1-ol, nerolidol 3,7-11-trimethyl-1,6,10-dodecatrien-3-ol, 3-methyl,6-(1-methylethenyl)-9-decen-1-ol acetate, (Z)-3-methyl-6-(1-methylethenyl)-3,9-decadien-1-ol acetate, (E)-3,9-methyl-6-(1-methylethenyl)-5,8-decadien-1-ol acetate, 3-methylene-7-methyl-octen-1-ol propionate, (Z)-3,7-dimethyl-2,7-octadien-1-ol propionate, (Z)-3,9-dimethyl-6-(1-methyl-ethenyl)-3,9-decadlien-1-ol propionate.

The compositions according to the invention comprise at least one UV absorber which is only sparingly miscible with water. These are to be understood as meaning substances which are capable of absorbing UV light, preferably UV radiation from surlight in a wavelength range of from 270 to 400 nm. Suitable substances are preferably liquid UV absorbers, such as 2-(2-hydroxyphenyl)-benzotriazoles of the formula

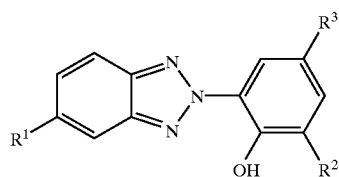

(I)

in which a $R^1$ represents hydrogen or chlorine, $R^2$ represents hydrogen, alkyl, phenylalkyl or phenyl and $R^3$ represents alkyl, phenylalkyl, phenyl or —$(CH_2)_2$—COO-alkyl, 2-hydroxy-4-alkoxy-benzophenones of the formula

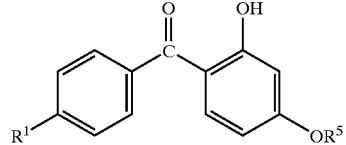

(II)

in which $R^4$ represents hydrogen, alkyl or alkoxy and $R^5$ represents alkyl, preferably isooctyl or dodecyl, oxalanilides of the formula

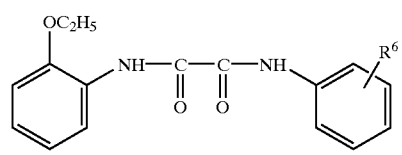

(III)

in which $R^6$ represents alkyl, cinnamic acid derivatives of the formula

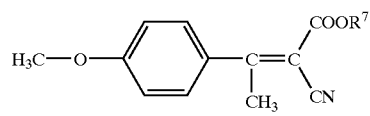

(IV-a)

in which $R^7$ represents alkyl, preferably n-butyl, or

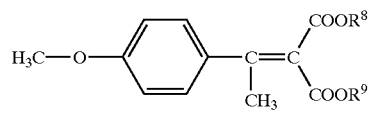

(IV-b)

in which $R^8$ and $R^9$ represent alkyl, or (IV-c)

in which $R^{10}$ represents alkyl, preferably butyl or the radical

—$CH_2$—$CH$—$C_4H_9$,
           |
          $C_2H_5$ and triazine derivatives of the formula (V)

in which $R^{11}$ represents hydrogen or hydroxyl, $R^{12}$ represents alkyl having 1 to 18 carbon atoms, $R^{13}$ represents alkyl having 1 to 18 carbon atoms or alkoxy having 1 to 18 carbon atoms, $R^{14}$ represents alkyl having 1 to 18 carbon atoms and m and n represent the numbers 0, 1 or 2.

Examples of 2-(2-hydroxyphenyl)-benzotriazoles of the formula (I) which may be mentioned are the substances listed in Table 1 below:

TABLE 1

(I)

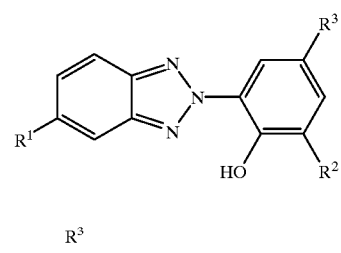

| Trade name | $R^1$ | $R^2$ | $R^3$ | |
|---|---|---|---|---|
| Tinuvin 109 | Cl | —C(CH$_3$)$_3$ | 50% | —CH$_2$—CH$_2$—C(=O)—O—C$_8$H$_{17}$ |

TABLE 1-continued

Structure (I): A benzotriazole with R¹ substituent on the benzene ring, N-linked to a phenyl ring bearing R³ (para), OH, and R² substituents.

| Trade name | R¹ | R² | R³ |
|---|---|---|---|
| | | | 50% —CH₂—CH₂—C(=O)—O—CH(C₂H₅)—C₄H₉ |
| Tinuvin 171 | H | —C₁₂H₂₅-(iso-mer mixture) | —CH₃ or C₂-C₁₂-alkyl |
| Tinuvin 1130 | H | —(CH₃)₃ | approx. 50% —CH₂—CH₂—C(=O)—O—(CH₂—CH₂—O)₃₀₀—H |
| | | | approx. 38% [—CH₂—CH₂—C(=O)—O—(CH₂—CH₂—O)₁₅₀—]₂ |
| | | | approx. 12% polyethylene glycol (EO 300) |
| "SL 874" | H | —C(CH₃)₃ | —CH₂—CH₂—C(=O)—O—(CH₂)₈—CH=CH—(CH₂)₇—CH₃ |

The compositions according to the invention comprise at least one unsaturated oil which is sparingly miscible with water. These are to be understood as meaning all straight-chain or branched oily liquids of synthetic or natural origin which optionally contain functional groups and which have one or more unsaturated bonds between two carbon atoms and whose solubility in water is <1 g/l.

Unsaturated oils are preferably of vegetable or animal origin and are distinguished by a high content of unsaturated fatty acids. Examples of such oils are linseed oil, palm oil, groundnut oil, cotton oil, soya oil, sunflower oil, colza oil, castor oil and fish oil. Castor oil is particularly preferred. However, the fatty acids contained in the abovementioned oils, or compounds which are obtained by chemically modifying the fatty acids such as, for example, fatty acid ethoxylates, can also be used to prepare the compositions according to the invention. Examples of such fatty acids which can be employed individually or in the form of a mixture are myristoleic acid, palmitoleic acid, oleic acid, gadoleic acid, erucic acid, ricinoleic acid, linoleic acid, linolenic acid, arachidonic acid and clupanodonic acid.

The compositions according to the invention can comprise one or more pesticidally active compounds. These are to be understood as meaning all customary substances which are suitable for controlling harmful insects and undesirable representatives of the order Acarina. The following are preferably suitable: carbamates, organophosphorus compounds, nitrophenols and their derivatives, nitromethylenes, nicotinoids, formamidines, ureas, phenylbenzoylureas, pyrethroids, chlorinated hydrocarbons and Bacillus thuringiensis preparations. Examples which may be mentioned are the following substances:

Abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, betacyfluthrin, bifenthrin, BPMC, bromfenprox, bromphos A, bufencarb, buprofezin, butocarboxim, butylpyridaben, cadusafos, carbaryl, carbofuran, carbophenothion, carbosulfan, cartap, CGA 157 419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazin, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos; dioxathion, disulfoton, edifenphos, emainectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycl.oxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin., lufenuron, malathion, mecarbam, mevinphos, mesulfenphos, metaldehyde, methacrifos, methamidophos, rnethidathion, methiocarb, methomyl, metolcarb, milbemectin, monocrotophos, mnxidectin, naled, NC 184, NI 25, nitenpyram ometohate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos,

RH 5992, salithion, sebufos, silafluofen, sulfotep, sulprofos, tebufenozid, tebu:Fenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathene, triazophos, triazuron, trichlorfon, triflumuron, trimelthacarb, vamidothion, XMC, xylylcarb, zetamethrin.

Suitable additives which may be present in the compositions according to the invention are all those substances which can conventionally be employed as additives in plant treatment products. They include polymers, surface-active substances, colourants, antioxidants, thickeners, fillers, antifreeze agents and solvents. Moreover, the compositions according to the invention can also contain water.

Suitable polymers which can be present in the compositions according to the invention are all customary polymers or copolymers which are soluble or dispersible in water. Preferably suitable are polymers which are accessible by synthesis by means of anionic or non-ionic polymerization of suitable monomers, for example by emulsion polymerization or bead polymerization with the aid of free-radical formers or other initiator systems. Other polymers which can preferably be employed are those based on natural-rubber latices.

Examples of particularly prefered polymers which may be mentioned are the following substances:

Polyvinyl acetate (Mowilith®), polyvinyl alcohols with different degrees of hydrolysis (Mowiol®), polyvinylpyrrolidones (Lewiskod K®, Agrimer®), polyacrylates (Carbopol®), acrylate-, polyol- or polyester-based paint system binders which are soluble or dispersible in water (Desmophen®, Roskydal®, Bayhydrol® polyraers which may be mentioned are the following substances:), moreover copolymers of two or more monomers such as acrylic acid, methacrylic acid, itaconic acid, maleic acid, fumaric acid, maleic anhydride, vinylpyrrolidone, ethylenically unsaturated monomers such as ethylene, butadiene, isoprene, chloroprene, styrene, divinylbenzene, ot-methylstyrene or p-methylstyrene, further vinyl halides such as vinyl chloride and vinylidene chloride, additionally vinyl esters such as vinyl acetate, vinyl propionate or vinyl stearate, moreover vinyl methyl ketone or esters of acrylic acid or methacrylic acid with monohydric alcohols or polyols such as methyl acrylate, methyl methacrylate, ethyl acrylate, ethylene methacrylate, lauryl acrylate, lauryl methacrylate, decyl acrylate, N,N-dimethylamino-ethyl methacrylate, 2-hydroxyethyl methacrylate, 2-hydroxypropyl methacrylate or glycidyl methacrylate, furthermore diethyl esters or monoesters of unsaturated dicarboxylic acids, furthermore (meth)acrylamido-N-methylol methyl ether, amides or nitriles such as acrylamide, methacrylamide, N-methylol (meth)acrylamide, acrylonitrile, methacrylonitrile, and also N-substituted maleiraides and ethers such as vinyl butyl ether, vinyl isobutyl ether or vinyl phenyl ether.

Suitable surface-active substances which can be present in the compositions according to the invention are all those substances which have surface-active properties and which are conventionally used in plant treatment products. Preferably suitable are non-ionic and anionic emulsifiers such as polyoxyethylene fatty acid esters, polyoxyethylene fatty alcohol ethers, alkylaryl polyglycol ethers, fatty amine ethoxylates, alkylsulphonates, alkyl sulphates, alkylarylsulphonates, aryl sulphates and silicone surfactants. Examples of such surface-active substances are listed in McCutcheon's "Emulsifiers and Detergents" 1982 North America Edit, MC Publishing Co., 175 Rock Road, Glen Rock, N.J. 07 452, USA.

Suitable colourants are soluble or sparingly soluble colour pigments such as, for example, titanium dioxide, colour black or zinc oxide.

Suitable antioxidants are all substances which can usually be employed for this purpose in plant treatment products. Sterically hindered phenols and alkyl-substituted hydroxyanisoles and hydroxytoluenes are preferred.

Suitable thickeners are all substances which can usually be employed for this purpose in plant treatment products. The following are preferably suitable: organic polymers such as partially or fully neutralized polyacrylic acids (Carbopol®), polyvinylpyrrolidone homo- or copolymers (Luviskol K® or Luviskol VA®), polyethylene glycols (Polyox®), ethylene oxide/propylene oxide copolymers (Pluronic®), polyvinyl alcohols and non-ionically or ionically modified celluloses (Tylose®), thixotropic xanthan-based thickeners (Kelzan®), and moreover inorganic disperse thickeners such as precipitated or pyrogenic silicas, kaolins, bentonites, aluminium/silicon mixed oxides, and silicates.

Suitable antifreeze agents are all substances which can usually be employed for this purpose in plant treatment products. Urea, glycerol or propylene glycol are preferably suitable.

Suitable fillers are, again, all inert materials which can usually be employed for this purpose in plant treatment products. The following are preferably suitable: ground minerals, calcium carbonate, ground quartz and aluminium/silicon mixed oxides or mixed hydroxides.

Suitable solvents are all inert, organic solvents which can usually be employed for this purpose in plant treatment products. Preferred substances are glycols such as propylene glycol and polyethylene glycols having various molecular weights; ketones such as methyl isobutyl ketone, methyl isopropyl ketone and cyclohexanone; amides such as dimethyl- or diethyl formamide; N,N-dialkylated carboxamides (for example Hallcomid®); alkyllactams such as substituted pyrrolidones (for example N-methylpyrrolidone and Surfadone®) and caprolactams (for example Azone®); hydrocarbons, n-paraffins and isoparaffins having various boiling ranges as can be obtained, for example, under the trade names Exxol®, Norpar® and Isopar®; aromatic hydrocarbons such as xylene and aromatic distillation fractions (for example Solvesso®); esters such as propylene glycol monomethyl ether acetate, dibutyl adipate and di-n-butyl phthalate; ethers such as propylene glycol methyl ether or propylene glycol butyl ether; alcohols such as ethanol, n- and i-propanol, n- and i-butanol, n- and i-amyl alcohol, benzyl alcohol, tetrahydrofurfuryl alcohol, 1-methoxy-2-propanol, and higher alcohols, furthermore liquid carriers which have been obtained by modifying vegetable oils, such as, for example, rapeseed oil methyl ester and 2-ethylhexyl laurate; and furthermore dimethyl sulphoxide, dioxane and tetrahydrofuran. The solvents can be employed in the form of individual components or in the form of mixtures. Particularly preferred are those which are miscible with the UV stabilizer or the unsaturated oil and which are not unduly volatile.

The concentrations of individual components in the compositions according to the invention can be varied within a wide range. For example, after deducting the water which is optionally present in the compositions according to the invention, the concentrations of signal substances are generally between 0.01 and 1% by weight, preferably between 0.05 and 0.3% by weight, of UV absorbers are generally between 1 and 40% by weight, preferably between 5 and 20% by weight, of unsaturated oils are between 10 and 90% by weight, preferably between 40 and 85% by weight, of pesticidally active compounds are generally between 0 and 10% by weight, preferably between 0 and 5% by weight, of additives are between 0 and 70% by weight, preferably between 0 and 60% by weight.

Besides, the compositions according to the invention can also comprise water. The water content prior to drying varies within a wide range. It is generally between 0 and 80% by weight.

When preparing the compositions according to the invention, a procedure is generally followed in which a premix is first prepared by dissolving or dispersing at least one signal substance, at least one UV absorber and, if appropriate, one or more pesticidally active compounds in at least one unsaturated oil with stirring at temperatures between 20° C. and 70° C., preferably at room temperature, and, if appropriate, additives are added. However, a different procedure may also be followed when preparing compositions according to the invention. For example, the premix can be dispersed in a solution of at least one surface-active substance in water with stirring at temperatures between 20° C. and 70° C., preferably at room temperature. The dispersing process can be carried out in such a way that an oil-in-water emulsion is formed in which the average particle size is generally between 0.5 and 50 $\mu$m, but preferably between 1 and 20 $\mu$m. The resulting emulsion can subsequently be treated with a solution or dispersion of at least one polymer in water and, if appropriate, additives with stirring at temperatures between 20° and 70° C., but preferably at room temperature.

However, a different procedure may be followed when preparing the compositions according to the invention. In principle, it is possible to mix the components in any order. All stirring and mixing apparatus which is customary for this purpose is suitable for preparing the compositions according to the invention.

The compositions according to the invention are obtained from the preparation in a fluid or viscous state. Depending on the preparation process, they remain viscous after application or else form a non-flowable coating.

The compositions according to the invention are highly suitable for controlling harmful insects and undesirable representatives of the order Acarina which are found in agriculture, in forests and in horticulture, including viticulture. For example, they can be employed against the pests mentioned below.

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria* migratorioides, *Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Phylloxera vastatrix,* Pemphigus spp., *Pediculus humanus corporis,* Haematopinus spp. and Linognathus spp.

From the order cf the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Bruchidius obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp.

From the order of the Arachnida, for example, *Scorpio maurus and Latrodectus mactans*.

From the order of the Acarina, for example, Acarus siro, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonivchus spp. and Tetranychus spp.

Using conventional devices as they are known to those skilled in the art the compositions according to the invention can be applied to, and distributed on, the areas under cultivation or plants to be treated in the form of droplets, the drop-size range or thin limited layers. Particularly suitable for the treatment of orchard crops or grape vines is a process in which a defined amount of the formulations according to the invention is applied to the stems of the plants with the aid of dosing dispensers, pipettes or syringes, it being possible for the application device also to be provided with a spreading device or a broad-jet nozzle so as to apply the compositions broadly over a relatively large area. It is also possible to spread the formulations according to the invention on a solid support, where they are allowed to dry.

The amounts in which the compositions according to the invention are applied can vary within a substantial range. They are in general in the order of magnitude which is conventionally used for "attract-and-kill" formulations.

The preparation and the use of compositions according to the invention is illustrated by the examples which follow.

PREPARATION EXAMPLES

Examples 1 to 5

The pheromone E,E-8,10-dodecadienol (=pheromone), the UV absorber 2-ethylhexyl 2-cyano-3,3-diphenyl-2-propenoate (=UV absorber A) and the UV absorber 2-hydoxy-4-methoxy-benzophenone (=UV absorber B) are dissolved with stirring at 50° C. in a 0.2% by weight solution of butylhydroxytoluene in castor oil (oil solution) in the amounts listed in Table 2

TABLE 2

| Ex. No. | Pheromone (g) | UV absorber A (g) | UV absorber B (g) | Oil solution (g) |
|---|---|---|---|---|
| 1 | 2 | 12.5 | 12.5 | 73.0 |
| 2 | 2 | 10.0 | 10.0 | 78.0 |
| 3 | 2 | 7.5 | 7.5 | 83.0 |
| 4 | 2 | 5.0 | 5.0 | 88.0 |
| 5 | 2 | 2.5 | 2.5 | 93.0 |

Example 6

2 g of the pheromone E,E-8,10-dodecadienot and 25.0 g of the benzotriazole of the formula

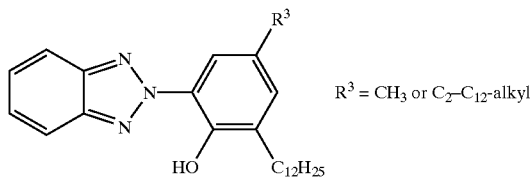

are dissolved at room temperature with stirring in 73 g of a 0.2% by weight solution of butylhydroxytoluene in castor oil.

Pheromone Stability Assessment

In each case 1 g of the formulations according to the invention of Examples 1 to 6 were placed into a round glass container of diameter 5 cm and covered with a sheet of quartz glass. In a Heraeus "Suntest CPS" rapid-exposure apparatus, the containers were exposed to light over a period of 6 days at a temperature of 40° C. The apparatus was equipped with a xenone lamp and provided an intensity of irradiation of 765 W/m$^2$ maximum. Twice daily, the containers were opened for 15 minutes in each case to allow air to enter. After the exposure, the residual content of the pheromone E,E-8,10-dodecadienol in the formulations according to invention was analyzed and the data used to calculate the percentage dation. The results are compiled in Table 3.

TABLE 3

| Example No. | Pheromone degradation (%) |
|---|---|
| 1 | 14.0 |
| 2 | 14.2 |
| 3 | 14.5 |
| 4 | 18.6 |
| 5 | 21.3 |
| 6 | 18.2 |

Example 7

0.03 g of E,E-8,10-dodecadienol, 0.04 g of butylhydroxytoluene, 2.0 g of 2-ethylhexyl 2-cyano-3,3-diphenyl-2-propenoate, 2.0 g of 2-hydroxy-4-methoxy-ophenone and 3.5 g of cyfluthrin are dissolved in 22 g of castor oil at 50° C. With the aid ofL a rotor/stator dispersing rod, this premix is emulsified at room temperature in a solution of 0.6 g of a castor oil ethoxylate of a mean degree of ethoxylation of 30 in 30 g of demineralized water. This emulsion is treated with of a 45% by weight aqueous dispersion of an emulsion polymer of acrylonitrile, buitadiene and methacrylic acid and with 7.43 g of demineralized water with stirring at room temperature. 2.5 g of hydroxyethylcellulose are subsequently stirred in. (This hydroxyethylcellulose has a dynamic viscosity of 4000 mPa.S at 20° C. at a concentration of 20 g/l in water.) After the mixture has been left to stand for 15 hours, it is stirred to give a homogeneous paste.

Comparison Example 1

2 g of the pheromone E,E-8,10-dodecadienol are dissolved at 50° C. in 98 g of the absorber 2-ethylhexyl 2-cyano-3,3-diphenyl-2-propenoate.

Comparison Example 2

2 g of the pheromone E,E-8,10-dodecadienol are dissolved at 50° C. in a mixture of 73 g of 2-ethylliexyl 2-cyano-3,3-diphenyl-2-propenoate and 25 g of 2-hydroxy-4-methoxy-benzophenol.

Comparison Example 3

3 g of the pheromone E,E-8,10-dodecadienol are dissolved at 50° C. in a mixture of 25 g of the benzotriazole of Example 6 and 73 g of a paraffin oil of boiling point >300° C. and a viscosity of 16 mm$^2$/sec.

Comparison Example 4

2 g of the pheromone E,E-8,10-dodecadienol are dissolved at 50° C. in 98 g of castor oil.

Pheromone Stability Assessment

The formulations of the Comparison Examples 1 to 4 were tested for pheromone degradation with exposure to UV as has been described above for the compositions of Examples 1 to 6. The results are compiled in Table 4.

TABLE 4

| Comparison Example No. | Pheromone degradation (%) |
| --- | --- |
| 1 | 96.3 |
| 2 | 87.4 |
| 3 | 98.0 |
| 4 | 99.9 |

Comparison Example 5

0.04 g of butylhydroxytoluene, 2.0 g of 2-ethylhexyl 2-cyano-3,3-diphenyl-2-propenoate, 2.0 g of 2-hydroxy-4-methoxy-benzophenone and 3.5 g of cyfluthrin are dissolved in 22 g of castor oil at 50° C. With the aid of a rotor/stator dispersing rod, this premix is emulsified at room temperature in a solution of 0.6 g of a castor oil ethoxylate of a mean degree of ethoxylation of 30 in 30 g of demineralized water. This emulsion is treated with 30 g of a 45% by weight aqueous dispersion of an emulsion polymer of acrylonitrile, butadiene and methacrylic acid and with 7.43 g of demineralized water with stirring at room temperature. 2.5 g of hydroxyethylcellulose are subsequently stirred in. (This hydroxyethylcellulose has a dynamic viscosity of 4000 mPa.S at 20° C. at a concentration of 20 g/l in water.) After the mixture has been left to stand for 15 hours, it is stirred to give a homogeneous paste.

Use Examples

Example A

Young apple trees of approximately 30 cm in size were treated on the stem, on one leaf on the upper side and on one leaf on the underside with the formulation according to the invention of Example 7 in the form of three drops approximately 50 microliters in size. The young trees together with 10 male specimens of the codling moth (*Cydia pomonella*) were shut into gauze cages. Four of these cages were positioned in a wind tunnel through which air was passed at a speed of 0.1 m/s. After 24 hours, the total of destroyed insects in the cages was determined. It was 50% of the animals originally introduced. In an experiment with the pheromone-free comparison formulation 5 which was carried out simultaneously, the percentage was only 12.5.

What is claimed is:

1. A pesticidal composition comprising the following ingredients:

a) 0.01 to 1 percent by weight of a signal substance having a solubility in water of less than 1 gram per liter or a mixture of such signal substances, said signal substance being selected from the group consisting of pheromones, kairomones, and attractants;

b) 1 to 40 percent by weight of a UV absorber or a mixture of UV absorbers selected from the group consisting of:

i) a benzotriazole of the formula:

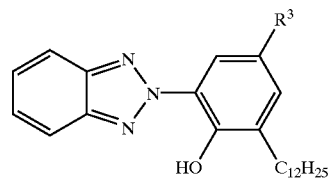

wherein
R$^3$ represents methyl or C$_2$–C$_{12}$-alkyl;

ii) 2-ethylhexyl-2-cyano-3,3-diphenyl-2-propenoate of the formula:

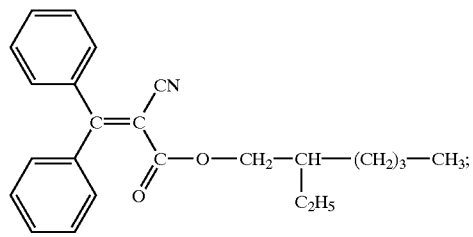

iii) 2-hydroxy-4-methoxy-benzophenone of the formula:

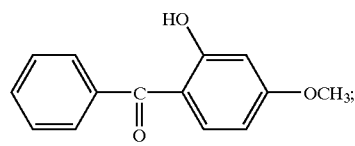

c) 40 to 90 percent by weight of castor oil;

d) a pesticidally effective amount of up to 10 percent by weight of at least one pyrethroid or a mixture of pyrethroids; and e) optionally 0 to 70 percent by weight of one or more additives selected from the group consisting of polymers, surface-active substances, colorants, antioxidants, thickeners, fillers, antifreeze agents, solvents and water;

wherein the percents by weight are based on the weight of the composition after deducting the weight of any water present therein.

2. A pesticidal composition as claimed in claim 1, wherein the UV absorber is 2-ethylhexyl-2-cyano-3,3-diphenyl-2-propenoate of the formula:

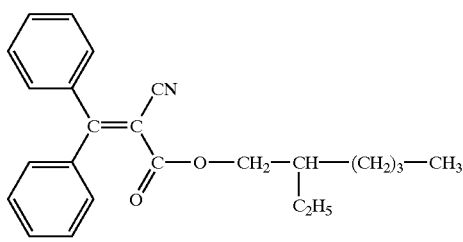

or 2-hydoxy-4-methoxy-benzophenone of the formula:

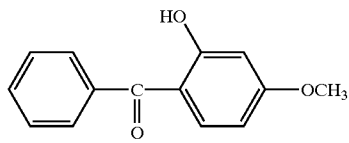

or a mixture of 2-ethylhexyl-2-cyano-3,3-diphenyl-2-propenoate and 2-hydroxy-4-methoxy-benzophenone.

3. A pesticidal composition as claimed in claim 1, wherein, after deducting the water which is present, the content of signal substance or signal substance mixture is between 0.05 and 0.3% by weight.

4. A pesticidal composition as claimed in claim 1, wherein, after deducting the water which is present, the content of UV absorber or UV absorber mixture is between 5 and 20% by weight.

5. A pesticidal composition as claimed in claim 1, wherein, after deducting the water which is present, the content of castor oil is between 40 and 85% by weight.

6. A pesticidal composition as claimed in claim 1, wherein, after deducting the water which is present, the content of pesticidally active compound or mixture of pesticidally active compounds is up to 5% by weight.

7. A pesticidal composition as claimed in claim 1, wherein, after deducting the water which is present, the content of additives is between 0 and 60% by weight.

8. A pesticidal composition as claimed in claim 1, wherein, after deducting the water which is present, the content of:

a) signal substance or signal substance mixture is between 0.05 and 0.3% by weight;

b) UV absorber or UV absorber mixture is between 5 and 20% by weight;

c) castor oil is between 40 and 85% by weight;

d) pesticidally active compound or a mixture of pesticidally active compound is up to 5% by weight; and e) additives is between 0 and 60% by weight.

9. A pesticidal composition as claimed in claim 1, wherein the pesticidally active compound is cyfluthrin.

10. A pesticidal composition as claimed in claim 1, wherein the pesticidally active compound is β-cyfluthrin.

11. A pesticidal composition as claimed in claim 1, wherein the signal substance is E,E-8,10-dodecadienol.

12. A pesticidal composition as claimed in claim 1, wherein the UV absorber is a benzotriazole of the formula

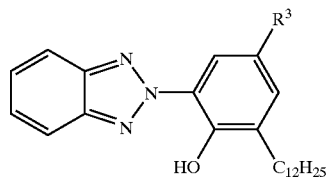

in which $R^3$ represents methyl or $C_2$–$C_{12}$-alkyl.

13. Method for controlling harmful insects and undesirable representatives of the order Acarina in agriculture, forestry and horticulture, which method comprises applying a composition as claimed in claim 1 to the habitat of said harmful insects and undesirable representatives of the order Acarina.

* * * * *